US008938106B2

(12) United States Patent
Aulbach et al.

(10) Patent No.: US 8,938,106 B2
(45) Date of Patent: Jan. 20, 2015

(54) METHOD AND DEVICE FOR IDENTIFYING AND ASSIGNING CORONARY CALCIFICATION TO A CORONARY VESSEL AND COMPUTER PROGRAM PRODUCT

(75) Inventors: Peter Aulbach, Forchheim-Kersbach (DE); Matthias Niethammer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 376 days.

(21) Appl. No.: 12/945,920

(22) Filed: Nov. 15, 2010

(65) Prior Publication Data

US 2011/0118595 A1 May 19, 2011

(30) Foreign Application Priority Data

Nov. 16, 2009 (DE) .......................... 10 2009 053 471

(51) Int. Cl.
*G06K 9/00* (2006.01)
*A61B 6/00* (2006.01)
(Continued)

(52) U.S. Cl.
CPC ....... *A61B 6/503* (2013.01); *G06T 2207/20141* (2013.01); *G06T 2207/10081* (2013.01); *G06T 7/0012* (2013.01); *G06T 2207/30048* (2013.01); *G06T 2207/20148* (2013.01); *A61B 6/032* (2013.01); *G06T 7/0081* (2013.01); *A61B 6/504* (2013.01); *G06T 2207/30101* (2013.01)
USPC .......................................... 382/131; 382/128

(58) Field of Classification Search
None
See application file for complete search history.

(56) References Cited

U.S. PATENT DOCUMENTS

| 7,751,984 B2* | 7/2010 | Tang ................................ 702/19 |
| 8,139,836 B2* | 3/2012 | Arnold et al. ................. 382/131 |
| 2003/0176780 A1 | 9/2003 | Reed | |

(Continued)

FOREIGN PATENT DOCUMENTS

| CN | 1781456 A | 6/2006 |
| CN | 101317766 A | 12/2008 |

(Continued)

OTHER PUBLICATIONS

H.-J. Trappe et al., "Natural history of single vessel disease. Risk of sudden coronary death in relation to coronary anatomy and arrhythmia profile", European Heart Journal (1989) 10, 514-524; Others; 1989.

(Continued)

*Primary Examiner* — Nancy Bitar
(74) *Attorney, Agent, or Firm* — Harness, Dickey & Pierce

(57) ABSTRACT

A method and a device are disclosed for identifying and assigning coronary calcification to at least one coronary vessel of a heart in a patient. In at least one embodiment, coronary calcification is identified on the basis of a 3D image data record of the heart in the patient, which data record was generated by an imaging instrument without contrast agent being administered; at least one 3D model of the profile of the coronary vessels in a human is provided; and wherein the identified coronary calcification in the patient is assigned to at least one coronary vessel of the at least one 3D model of the profile of the coronary vessels in a human. At least one embodiment moreover relates to a computer program product, having a computer program that is stored on a medium that can be read by a computational unit, for carrying out the method for identifying and assigning coronary calcification when the computer program is loaded into the computational unit.

20 Claims, 2 Drawing Sheets

(51) Int. Cl.
*G06T 7/00* (2006.01)
*A61B 6/03* (2006.01)

(56) References Cited

U.S. PATENT DOCUMENTS

| | | | |
|---|---|---|---|
| 2003/0215124 A1* | 11/2003 | Li | 382/131 |
| 2005/0228261 A1* | 10/2005 | Huber et al. | 600/410 |
| 2006/0122500 A1 | 6/2006 | Heismann et al. | |
| 2006/0149522 A1* | 7/2006 | Tang | 703/11 |
| 2006/0253021 A1* | 11/2006 | Aharon | 600/416 |
| 2007/0248261 A1* | 10/2007 | Zhou et al. | 382/154 |
| 2008/0094398 A1 | 4/2008 | Ng et al. | |
| 2008/0159610 A1* | 7/2008 | Haas et al. | 382/131 |
| 2008/0304728 A1 | 12/2008 | Licato et al. | |
| 2009/0136107 A1* | 5/2009 | Arnold et al. | 382/131 |
| 2010/0156898 A1* | 6/2010 | Voros et al. | 345/419 |
| 2010/0278405 A1* | 11/2010 | Kakadiaris et al. | 382/131 |
| 2011/0243412 A1* | 10/2011 | Grass et al. | 382/131 |
| 2012/0028881 A1* | 2/2012 | Wilkins et al. | 514/1.9 |

FOREIGN PATENT DOCUMENTS

| | | |
|---|---|---|
| CN | 101405769 A | 4/2009 |
| DE | 10 2009 053 471.1 | 11/2009 |
| WO | WO 2008135946 A2 | 11/2008 |

OTHER PUBLICATIONS

Kawaharada T., "Long-Term Prognosis in Patients With Single-Vessel or Double-Vessel Coronary Artery Disease: Does Successful Revascularization Achieved by Coronary Angioplasty Improve Late Outcome?", J. Cardiol Jul. 2003; 42(I): 1-11; Others; 2003.

Chinese Office Action and English translation thereof dated Feb. 7, 2014.

Chen, Yun-Dai; "Basic Equipment Used in Coronary Intervention (1)"; in China Medical Device Information, 2007; vol. 13, No. 4 pp. 1-17; 2007; CN.

Office Action for corresponding Chinese Application No. 201010549955.4 dated Sep. 3, 2014 and English translation thereof.

* cited by examiner ent application hereby claims priority under 35
METHOD AND DEVICE FOR IDENTIFYING AND ASSIGNING CORONARY CALCIFICATION TO A CORONARY VESSEL AND COMPUTER PROGRAM PRODUCT

PRIORITY STATEMENT

The present application hereby claims priority under 35 U.S.C. §119 on German patent application number DE 10 2009 053 471.7 filed Nov. 16, 2009, the entire contents of which are hereby incorporated herein by reference.

FIELD

At least one embodiment of the invention generally relates to a method and/or a device for identifying and assigning coronary calcification to a coronary vessel of a heart in a patient. At least one embodiment of the invention moreover generally relates to a computer program product having a computer program for carrying out the method.

BACKGROUND

Cardiac and cardiovascular diseases are very widespread in western industrial nations. By way of example, these days a quarter of German citizens suffer from high blood pressure and each year approximately 400 000 German citizens suffer a myocardial infarction or cerebrovascular accident, the main cause of which is arteriosclerosis. Arteriosclerosis is understood to be a disease of the arteries, in which, inter alia, calcium is deposited on the inner walls of the arteries. If the calcium seals off e.g. a coronary vessel, this can result in a myocardial infarction.

The so-called calcification score has been established for estimating the risk a patient has of suffering a myocardial infarction. By way of example, in order to establish the calcification score, image information relating to the heart in a patient is obtained by X-ray computed tomography and the calcification score for the patient is determined from the image information, i.e. the amount of coronary calcification in the region of the heart registered by the image information. According to Agatston's method, calcified regions in the image information are in the process initially marked by hand. A computer program then calculates the calcification score on the basis of the marked calcified regions.

The calcification score in humans with healthy coronary arteries varies with age and sex. Therefore, in order to be able to undertake an individual risk assessment, it is necessary to compare the measured calcification score to a comparison group of the same sex and the same age. This is carried out in the form of so-called percentiles. Low percentiles correspond to a low personal risk, high percentiles to a high risk. By way of example, a calcification score below the 10th percentile means that less than 10% in the comparison group have a lower calcification score; the risk of a myocardial infarction thus is low.

The classification of a patient's risk can for example be carried out on the basis of a table. Hereinbelow, such a table is indicated in merely an example fashion:

| Coronary calcification score (Agatston) | Assessment of the coronary sclerosis | Risk assessment |
|---|---|---|
| 0-10 | None/minimal | Low risk |
| 11-100 | Moderate | Moderate risk |
| 101-400 | Significant | Increased risk |
| 401-1000 | Pronounced | High risk |

Someone is considered a risk patient if their value lies above the 75th percentile, corrected for age and sex. It thus is a relative value compared to that of an overall population. In the case of unfavorable values, cardiologists suggest a significant decrease in low density lipoproteins (LDL) because a high calcification score is connected with a medium to high risk of developing cardiovascular disease within the next 2 to 5 years.

The calcification score is generally obtained on the basis of a cardiac scan using X-ray computed tomography, during which no contrast agent is administered to the patient. Thus it is difficult in anatomical terms to assign the determined coronary calcification to the coronary vessels because the coronary vessels lack contrast in the image information. Thus, the calcification score merely specifies how much coronary calcification is present in the coronary vessels, but does not differentiate the number of the four main coronary vessels in which the coronary calcification was measured.

Although this information could be obtained using so-called coronary CT angiography, it cannot be used per se for determining the calcification score because a contrast agent has to be administered to the patient and the work has to be undertaken at a higher radiation dose. Whereas the radiation dose for a CT scan for determining the calcification score is approximately 0.8 mSv, the radiation dose in coronary CT angiography lies between approximately 4 and 20 mSv.

However, the differentiation according to the number of coronary vessels in which the calcification score was measured or how the coronary calcification is distributed over the coronary vessels has a decisive influence on assessing the risk for the patient. If the assumption is made that the calcification score recorded by X-ray computed tomography is constant, it immediately becomes apparent that the concentration of this calcification volume in only one coronary vessel has much more drastic effects on the blood supply of the heart than a more even distribution of the coronary calcification to all four coronary vessels.

SUMMARY

At least one embodiment of the invention specifies a method, a device and/or a computer program product such that identified coronary calcification can be assigned to at least one coronary vessel on the basis of a 3D image data record of the heart in a patient, which data record was generated without contrast agent being administered.

According to at least one embodiment of the invention, a method is disclosed for identifying and assigning coronary calcification to at least one coronary vessel of a heart in a patient, in which coronary calcification is identified on the basis of a 3D image data record of the heart in the patient, which data record was generated by an imaging instrument without contrast agent being administered, in which at least one 3D model of the profile of the coronary vessels in a human is provided, and in which the identified coronary calcification in the patient is assigned to at least one coronary vessel of the at least one 3D model of the profile of the coronary vessels in a human.

In at least one embodiment, the 3D image data record may be for example, but not necessarily, obtained by an X-ray computed tomography scanner or another type of X-ray scanner, for example a C-arm X-ray scanner, and the heart is isolated from the tissue surrounding the heart in the 3D image data record, for example by removing ribs of the rib cage or lung tissue contained in the image data record from the image data record. The 3D image data record preferably only having cardiac tissue is subsequently searched for high-contrast coronary calcification in an automated fashion, and found coronary calcification is identified as such, for example on the basis of characteristic CT values.

Since the lack of contrast due to abstaining from using a contrast agent leads to it being difficult or impossible to identify, in the 3D image data record, the coronary vessels of the heart in the patient, at least one embodiment the inventors propose the provision of a general 3D model of the profile of the coronary vessels in a human so as to be able to assign the identified coronary calcification to a coronary vessel. A comparison between the spatial arrangement of the identified coronary calcification and the 3D model of the profile of the coronary vessels in a human allows, for example by using pattern recognition techniques, overlaying of the spatial arrangement of the identified coronary calcification onto the 3D model of the profile of the coronary vessels in a human, for example using rotational, displacement or translational operations, such that the identified coronary calcification can be assigned to at least one coronary vessel in the 3D model.

This affords the possibility of distinguishing between a so-called "single vessel disease (SVD)", a "2 vessel disease (2VD)", a "3 vessel disease (3VD)" and a "4 vessel disease (4VD)", that is to say whether there is coronary calcification in only one, two, three or four coronary vessels, which has a large influence on the assessment of the risk to a patient suffering a myocardial infarction due to deposited coronary calcification.

This was already established scientifically in 1989 in a study by H.-J. Trappe et al., "Natural history of a single vessel disease. Risk of sudden coronary death in relation to coronary anatomy and arrhythmia profile", European Heart Journal 1989 10(6): 514-524, the entire contents of which are hereby incorporated herein by reference. The team of scientists led by Trappe discovered that there was a significant risk of sudden coronary death as a result of "single vessel disease". Considered in terms of individual coronary arteries, this means that the risk of a sudden coronary death in the case of "single vessel disease" is approximately 11% in the left coronary artery,
    approximately 8% in the right coronary artery, and
    approximately 7% in the left circumflex.

Incidentally, when coronary calcification is discussed here, this does not mean that coronary calcification relates to a particular form of deposited calcium. The term coronary calcification should merely express that this relates to calcium deposited in coronary vessels.

According to one variant of at least one embodiment of the invention, the at least one 3D model of the profile of the coronary vessels in a human comprises as coronary vessels the right coronary artery (RCA), the left coronary artery (LCA), the left circumflex artery (LCX) and the left anterior descending artery (LAD) of the heart. Here, the left coronary artery divides into the left circumflex artery and the left anterior descending artery after approximately 1 cm. The aforementioned main coronary vessels have further branches that can likewise be included in the 3D model of the profile of the coronary vessels in a human.

One embodiment of the invention provides for the at least one 3D model of the profile of the coronary vessels in a human to be an artificially generated 3D model based on expert knowledge of anatomy or a 3D model generated on the basis of a multiplicity of measured 3D data records of hearts with coronary vessels from a number of humans. Thus, the 3D model can be a 3D model programmed on the basis of expert knowledge in the art, in which the spatial coordinates of, in particular, the center lines and enveloping curves, or vessel walls, of the coronary vessels are stored in a data storage medium.

Alternatively, the 3D model is the result of a multiplicity of cardiac measurements. Thus, for example, several hundred coronary CT angiography data records from different people can be evaluated in respect of the position and profile of the center lines and the position, form and shape of the vessel walls of the coronary vessels in order to develop a general 3D model therefrom, in which model the spatial coordinates of, in particular, the center lines and enveloping curves, or vessel walls, of the coronary vessels are in turn stored in a data storage medium.

Moreover, there is the option of keeping a number of such 3D models, which can also have anatomical peculiarities, available in a data storage medium. More particularly, the is the option of maintaining a 3D model for women and a 3D model for men, and there is the option of scaling, more particularly adjusting the model to the size of the heart of the patient to be examined. The best-suited 3D model can then be used for the evaluation in the method according to the invention.

A further embodiment of the invention provides for the option of prescribing, or the prescription of, the diameter of a coronary vessel or the change in the diameter of a coronary vessel along the profile of the coronary vessel in the at least one 3D model of the profile of the coronary vessels in a human. Since the diameter of a coronary vessel or the change in the diameter of a coronary vessel along the profile of the coronary vessel can be adjusted by a user, the sensitivity of the method according to at least one embodiment of the invention or of the 3D model can be set. Thus, selecting a relatively small diameter of a coronary vessel in the 3D model results in a high sensitivity because there is a low probability of an erroneous assignment of coronary calcification to the relevant coronary vessel. By contrast, the sensitivity is rather low in the case where a relatively large diameter is selected for a coronary vessel in the 3D model because the probability increases of assigning coronary calcification to the coronary vessel concerned even though the coronary calcification is actually situated outside of the coronary vessel concerned.

According to one variant of at least one embodiment of the invention, the 3D image data record of the heart in the patient has a plurality of slice images, situated one behind the other in the axial direction, of the heart comprising pixels. As mentioned previously, a 3D data record comprising such axial slice images can for example be obtained using X-ray computed tomography.

According to further variants of at least one embodiment of the invention, those pixels that represent coronary calcification in a slice image of the 3D image data record are preferably identified in an automated fashion. In the case of a 3D image data record generated by X-ray computed tomography, this can, for example, be achieved by fixing one or more thresholds for CT values. If the CT value of a pixel in a slice image lies above the fixed threshold, the respective pixel represents coronary calcification and is classified as such. The process of identifying pixels that represent coronary calcification is effected in all slice images of the 3D image data record.

Once the pixels that represent coronary calcification have been identified, mutually adjacent pixels that represent coronary calcification are interconnected within a slice image and across slice images or are associated with one another. At least one spatial accumulation, in general a plurality of spatial accumulations, of pixels that represent coronary calcification is, or are, obtained in this fashion.

According to a variant of at least one embodiment of the invention, pixels that are at a distance of between one and thirty pixels from an initial pixel that represents coronary calcification are in the neighborhood of the initial pixel. Hence, once an initial pixel has been identified as a pixel that represents coronary calcification, neighboring pixels that represent coronary calcification are sought after, and an accumulation of pixels that represent coronary calcification is defined or fixed on the basis of neighboring pixels that represent coronary calcification. Here, the search region can be prescribed in respect of distance from the pixels, with the search preferably being conducted in a region around an initial pixel, in which the pixels to be examined have a distance of up to six pixels to up to fifteen pixels.

As mentioned above, the grouping together of pixels that represent coronary calcification results in spatial accumulations. As a result, each spatial accumulation or all spatial accumulations of pixels that represent coronary calcification can be related or compared to the at least one 3D model of the profile of the coronary vessels in a human, and so the spatial accumulations of pixels that represent coronary calcification and the at least one 3D model of the profile of the coronary vessels in a human can be overlaid on the basis of rotational, displacement and/or translational operations. This is preferably brought about by a similarity comparison, and so the coronary calcification identified by this overlay can be assigned to at least one coronary vessel in the 3D model.

If the 3D image data record is available as a data record of voxels, those voxels that represent coronary calcification in the 3D image data record of the heart in the patient are identified. In accordance with the procedure as described above for the slice images with pixels, mutually adjacent voxels that represent coronary calcification are interconnected, or are associated with one another, and form at least one spatial accumulation of voxels that represent coronary calcification.

Voxels that are at a distance of between one and thirty voxels from an initial voxel that represents coronary calcification are preferably in the neighborhood of the initial voxel. Preferably, the distance range of voxels, in which further voxels that represent coronary calcification should be sought after, around an initial voxel that represents coronary calcification can or is prescribed in turn.

Once the voxels in the 3D image data record that represent the coronary calcification have been identified and at least one accumulation of voxels that represent coronary calcification has been formed, the spatial profile of the at least one accumulation of voxels that represent coronary calcification and the at least one 3D model of the profile of the coronary vessels in a human are related to one another or are compared to one another. Preferably, the at least one accumulation of voxels that represent coronary calcification is assigned to at least one coronary vessel in the at least one 3D model of the profile of the coronary vessels in a human on the basis of a similarity comparison between the spatial profile of the at least one accumulation of voxels that represent coronary calcification and the at least one 3D model of the profile of the coronary vessels in a human.

According to one embodiment of the invention, the at least one 3D model of the profile of the coronary vessels in a human and the identified coronary calcification in the patient, which coronary calcification is assigned to the at least one coronary vessel of the at least one 3D model of the profile of the coronary vessels in a human, are visualized, and so a user can identify the number of coronary vessels between which the identified coronary calcification is distributed.

According to a further embodiment of the invention, the volume of coronary calcification per coronary vessel is moreover established and output, and so a quantitative statement about the amount of coronary calcification per coronary vessel can also be made in addition to the distribution of the coronary calcification between the coronary vessels.

At least one embodiment of the present invention is further directed to a device having a storage unit for storing a 3D image data record of the heart in a patient and a 3D model of the profile of the coronary vessels in a human, and also having a computational unit for carrying out one of the above-described methods.

At least one embodiment of the present invention is further directed to a computer program product, having a computer program that is stored on a medium that can be read by the computational unit for carrying out one of the above-described methods when the computer program is loaded into the computational unit.

BRIEF DESCRIPTION OF THE DRAWINGS

An example embodiment of the invention is illustrated in the attached schematic drawings, in which.

DETAILED DESCRIPTION OF THE EXAMPLE EMBODIMENTS

Figure 1:
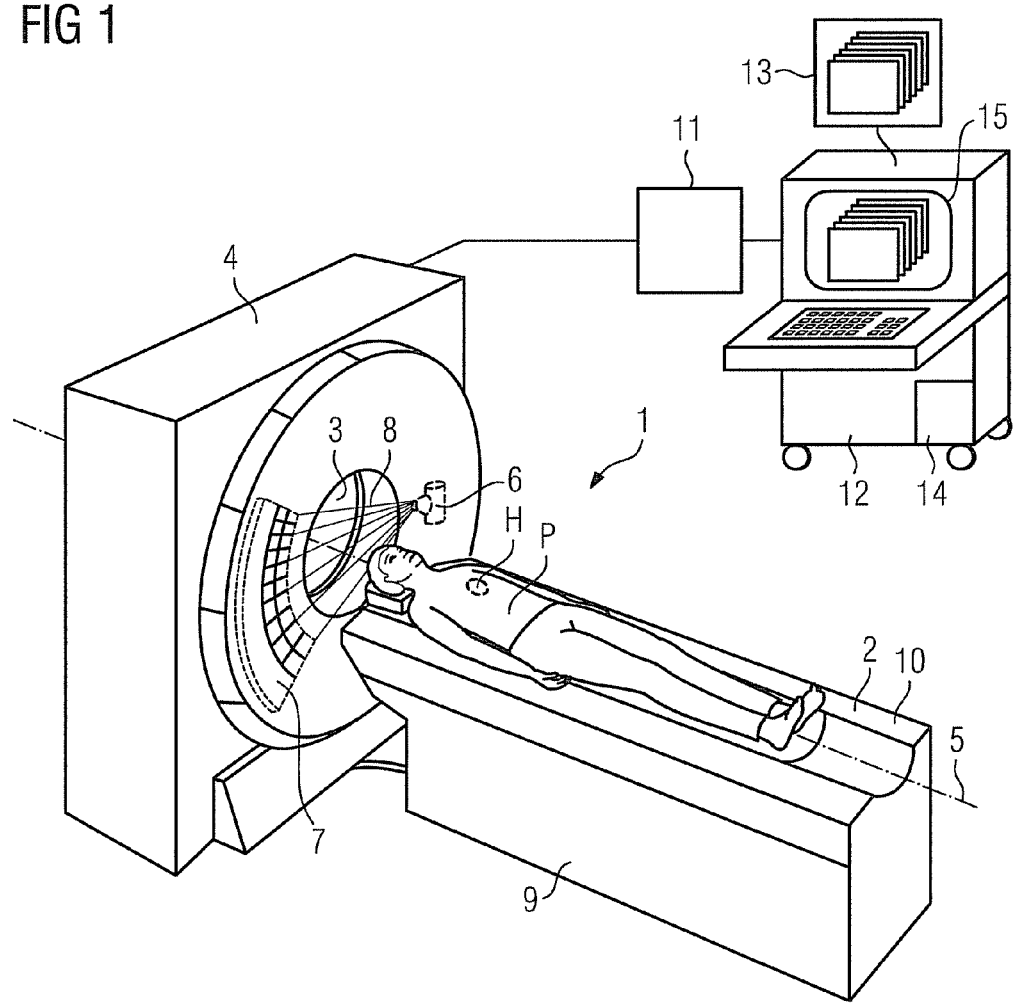
FIG. 1 shows, connected to a computational unit, an X-ray computed tomography scanner for generating a 3D image data record.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, equivalent or functionally equivalent elements, components, tissues, etc. have always been provided with the same reference sign. The illustrations in the figures are schematic and not necessarily to scale, wherein the scale can vary between the figures. In the following text, the X-ray computed tomography scanner 1 illustrated in FIG. 1 is only discussed to the extent that is considered necessary for understanding an embodiment of the invention, without restricting the generality as discussed above.

The X-ray computed tomography scanner 1 shown in figure has a patient couch 2 for supporting a patient P to be examined. The X-ray computed tomography scanner 1 furthermore comprises a gantry 4 with a tube-detector system mounted such that it can rotate about a system axis 5. The tube-detector system has an X-ray tube 6 and an X-ray detector unit 7, which mutually oppose one another. During operation, X-ray radiation 8 is emitted by the X-ray tube 6 in the direction of the X-ray detector unit 7, and is registered by the latter.

The patient couch 2 has a couch base 9, on which a patient support plate 10 provided for actually supporting the patient P is arranged. The patient support plate 10 can be adjusted relative to the couch base 9 such that the patient support plate 10 with the patient P can be introduced into the opening 3 of the gantry 4 for recording 2D X-ray projections of the patient P, e.g. in a spiral scan. The computational processing of the 2D X-ray projections, or the reconstruction of a 3D image data record of a body region of the patient P on the basis of the 2D X-ray projections, is brought about using a schematically illustrated image computer 11 of the X-ray computed tomography scanner 1.

The image computer 11 of the X-ray computed tomography scanner 1 is connected to a computational unit 12, which in the case of the present example embodiment of the invention should examine the coronary vessels of the heart in the patient P for the presence of coronary calcification. To this end, the computational unit 12 has been provided with an appropriate computer program 13, which, in the present case, was loaded into the computational unit 12 using a portable storage medium, for example a CD, and has program codes, segments and/or modules for evaluating a 3D image data record of a heart in order to identify coronary calcification and program codes, segments and/or modules for assigning the identified coronary calcification to coronary vessels. The computer program also comprises at least one general 3D model of the profile of the coronary vessels in a human, which is stored in a storage unit 14 of the computational unit 12 when the computer program 13 is loaded into the computational unit 12 and is maintained for assigning coronary calcification to the coronary vessels.

In order to be able to examine the coronary vessels in the patient P for the presence of coronary calcification, a 3D image data record of the heart H in the patient P is first of all generated in the case of the present example embodiment. For this purpose, 2D X-ray projections of the body region in the patient P containing the heart H are obtained from different projection directions under rotation of the tube-detector system in a spiral scan under continuous adjustment in the direction of the system axis 5 of the patient support plate with the patient P. As in a conventional CT scan for establishing the calcification score in a patient, no contrast agent was administered to the patient P in the process. On the basis of the recorded 2D X-ray projections, the image computer 11 reconstructs a 3D image data record of the body region in the patient P containing the heart H and the data record is stored in the storage unit 14 of the computational unit 12 for further evaluation. In the case of the present example embodiment, the 3D image data record is composed of a multiplicity of CT slices or slice images comprising pixels. By way, the 3D image data record comprises approximately 250 slice images, each with a slice thickness of approximately 0.6 mm.

In the case of the present example embodiment, the reconstructed 3D image data record is initially segmented according to tissues or organs. Subsequently the image information of the tissues surrounding the heart, e.g. lung tissue, ribs, etc. is removed from the 3D image data record. The heart is isolated, so to speak, in the 3D image data record. The segmentation can be brought about by hand, in a semi-automated fashion or in a fully-automated fashion.

The 3D image data record with image information relating to the heart is examined in an automated fashion, slice image by slice image, for the presence of high-contrast coronary calcification. In the simplest case at least one CT threshold is fixed for this purpose. If the CT value of a pixel in a slice image exceeds the CT threshold, the pixel is recorded as a pixel that represents coronary calcification. The automated identification of pixels that represent coronary calcification is comparatively unproblematic because high-contrast coronary calcification needs to be identified in low-contrast cardiac tissue.

Figure 2:
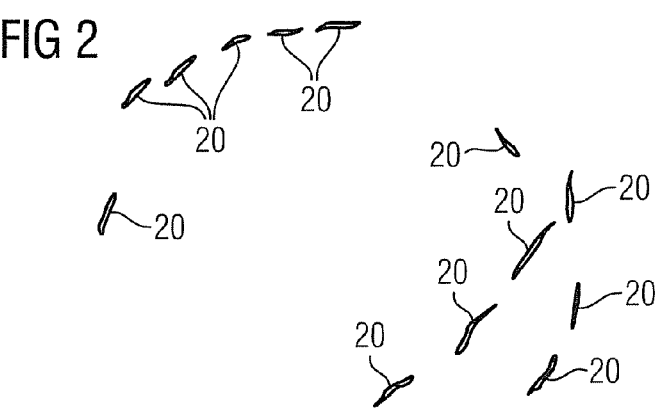
FIG. 2 shows spatial accumulations of coronary calcification identified in the 3D image data record.

Once the pixels that represent coronary calcification in the slice images have been identified, these are combined to form accumulations of pixels that represent coronary calcification. This is brought about as follows: starting from an initial pixel that represents coronary calcification, the neighborhood of this initial pixel is searched for further pixels that represent coronary calcification. Preferably, further pixels that represent coronary calcification are sought after, which are at a distance of no more than six to fifteen pixels away from the initial pixel. Here, the search is not only conducted within a slice image, but also across slice images. This is how neighboring pixels that represent coronary calcification are interconnected, associated with one another or combined to accumulations, which generally have a spatial profile. FIG. 2 illustrates such spatial accumulations 20 of identified pixels that represent coronary calcification in the 3D image data record in an example fashion.

Since the 3D image data record of the heart H in the patient P was generated without a contrast agent being administered, the coronary vessels of the heart H in the patient P cannot be identified, or can only be identified poorly, in the 3D image data record, and so it is not possible to assign the accumulations 20 to the individual coronary vessels. At this point of time in the method, all that can merely be stated is the calcification score for the patient P in a conventional fashion on the basis of the identified pixels that represent coronary calcification for the whole heart.

Figure 3:
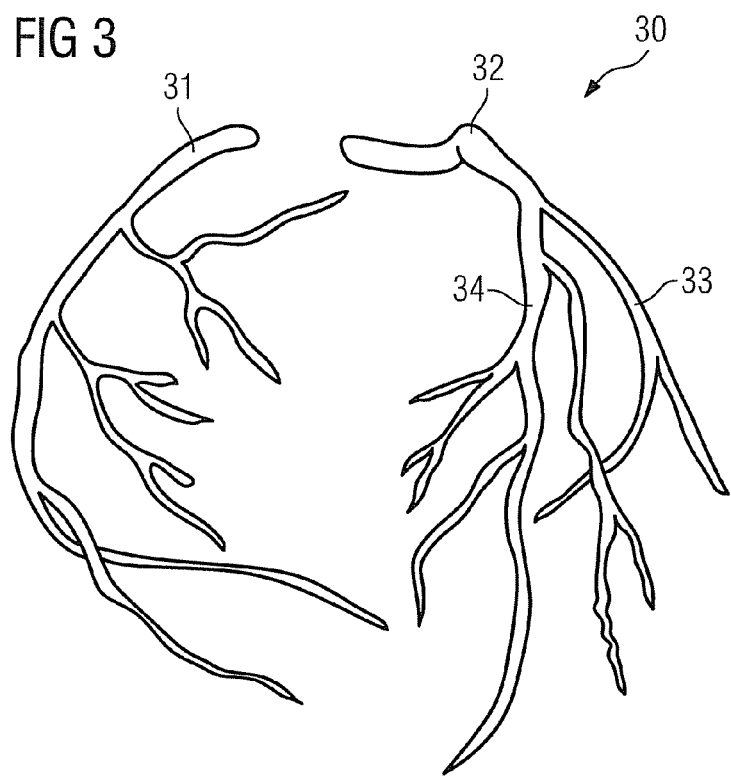
FIG. 3 shows a 3D model of the profile of the coronary vessels in a human.

So as also to be able to assign the identified coronary calcification to the coronary vessels, use is made of the aforementioned 3D model of the profile of the coronary vessels in a human. Such a 3D model 30 is illustrated in FIG. 3 in an example fashion. In the case of the present example embodiment of the invention, the 3D model of the profile of the coronary vessels in a human has as coronary vessels the right coronary artery 31 (arteria coronaria dextra), the left coronary artery (arteria coronaria sinistra), the left circumflex artery (LCX) 33 (ramus circumflexus) and the left anterior descending artery (LAD) 34 (ramus interventricularis anterior) of a heart. Here FIG. 3 shows that the left coronary artery 32 divides into the left circumflex artery 33 and the left anterior descending artery 34 after approximately 1 cm. The aforementioned coronary vessels in the 3D model have further branches, but these are not denoted in any more detail in the case of the present example embodiment of the invention.

The 3D model can be produced on the basis of expert knowledge of anatomy, virtually in an artificial fashion, or else can be the result of evaluating a multiplicity of measured 3D data records of the heart with coronary vessels from a number of different people. In both cases, the 3D model comprises the spatial coordinates of the center lines and the enveloping curves, or the vessel walls, of the coronary vessels 31 to 34 for a typical, average coronary anatomy.

Moreover, it is possible to keep a plurality of 3D models of the spatial profile of the coronary vessels available in the storage unit 14 and use these for the further evaluation, or to select them as needed. Thus, it is possible to keep available different 3D models for women and men or else 3D models with anatomical peculiarities.

Even if only one 3D model is kept available in the storage unit 14, an example embodiment of the invention provides for the option of prescribing the diameter of a coronary vessel or the change in the diameter of a coronary vessel along the spatial profile of the coronary vessel in the 3D model in order to fix the sensitivity of the assignment of an accumulation of pixels that represent coronary calcification to a coronary vessel. A relatively large selected diameter of for example 10 mm for a particular coronary vessel reduces the sensitivity because many accumulations of pixels that represent coronary calcification may be assigned to the particular coronary vessel. By contrast, a relatively small selected diameter for a particular coronary vessel of approximately 4 mm increases the sensitivity because the probability of an erroneous assignment of coronary calcification to the particular coronary vessel is reduced.

Figure 4:
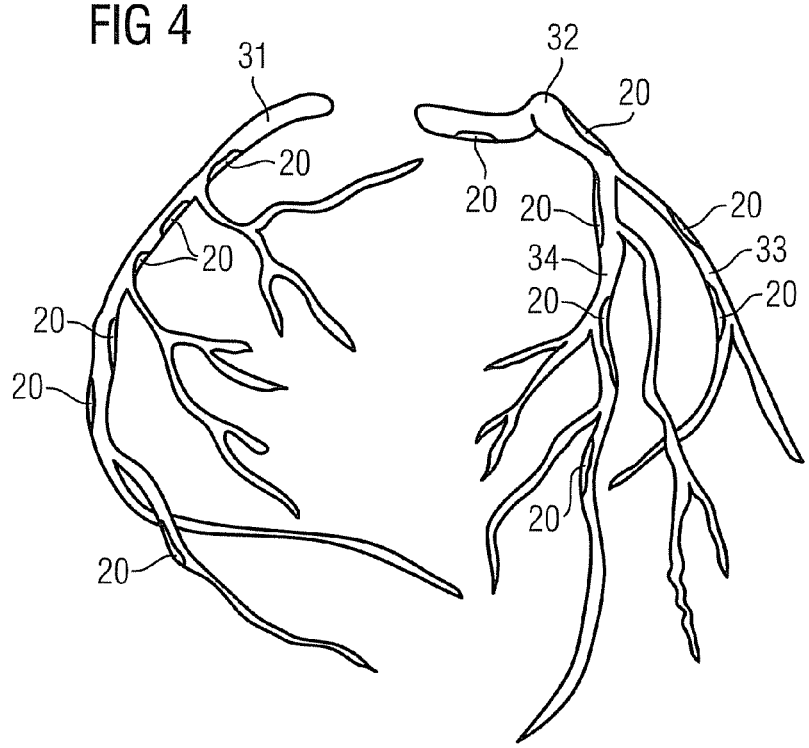
FIG. 4 shows the assignment of the spatial accumulations of coronary calcification identified in the 3D image data record in FIG. 2 to the 3D model of the profile of the coronary vessels in a human in FIG. 3.

When adjusting it to the measurement of the 3D image data record, the 3D model can generally be scaled in terms of its size. In the case of the present example embodiment of the invention, there is, in the end, a similarity comparison between the spatial profiles of the accumulations 20 of pixels that represent coronary calcification and the spatial profiles of the coronary vessels in the 3D model. In the process, use may also be made of pattern recognition techniques. By way of example, the 3D model 30 is aligned such that as many accumulations 20 of pixels that represent coronary calcification as possible, ideally all, can be assigned to a coronary vessel in the 3D model 30, i.e. lie within a coronary vessel in the 3D model, by rotational, displacement and/or translational operations. This situation is illustrated in FIG. 4.

This assignment affords the possibility of not only visualizing on a viewing instrument 15 which coronary vessels have coronary calcification, but also specifying the content of coronary calcification per coronary vessel, or the calcification volume per coronary vessel, by determining the volumes in the respective coronary vessels of the accumulations of pixels that represent coronary calcification and by outputting these on the viewing instrument next to the calcification score established in a conventional fashion.

Since the center lines of the coronary vessels are known from the 3D model of the profile of the coronary vessels, it is moreover possible to calculate and illustrate so-called "curved multi-planar reformats" for representing the coronary vessels. Hence the respective coronary vessel and its profile can be illustrated as in conventional coronary CT angiography, wherein the respective coronary vessel is shown with its calcification.

The method was described above for a 3D image data record comprising a plurality of slice images with pixels. However, the 3D image data record can also be a data record having voxels and this does not change the principle of the procedure. The difference is merely that the values of the voxels rather than of the pixels are evaluated, the voxels that represent coronary calcification are combined in a corresponding fashion to accumulations of voxels that represent coronary calcification and the spatial profile of these accumulations is compared to the 3D model of the profile of the coronary vessels in a human with the intent of assigning the accumulations to at least one coronary vessel in the 3D model.

Moreover, the 3D image data record of the heart in the patient does not necessarily have to be generated by an X-ray computed tomography scanner. Rather, the 3D image data record can also be generated by a C-arm X-ray scanner or else by a magnetic resonance imaging scanner.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for identifying and assigning coronary calcification to at least one coronary vessel of a heart in a patient, the method comprising:
   identifying pixels representing coronary calcification based on a 3D image data record of the heart in the patient, the 3D image data record being previously generated by an imaging instrument without a contrast agent being administered to the patient;
   determining spatial accumulation of the identified pixels;
   generating at least one 3D model of a profile of the coronary vessels in a human including spatial coordinates of centerlines and enveloping curves of the coronary vessels, the at least one 3D model depicting a right coronary artery, a left coronary artery, a left circumflex artery and a left anterior descending artery of the heart, the at least one 3D model being generated on a basis of a multiplicity of 3D data records of hearts with coronary vessels generated from a number of humans; and
   assigning the determined spatial accumulation of the identified pixels representing coronary calcification to the at least one 3D model of the profile of the coronary vessels in a human for distinguishing between a single vessel disease (SVD), a two vessel disease (2VD), a three vessel disease (3VD) and a four vessel disease (4VD).

2. The method as claimed in claim 1, further comprising:
   prescribing a diameter of the at least one coronary vessel or a change in the diameter of the at least one coronary vessel along the profile of the coronary vessel in the at least one 3D model of the profile of the coronary vessels in a human.

3. The method as claimed in claim 1, wherein the 3D image data record of the heart in the patient includes a plurality of slice images, situated one behind the other in an axial direction, of the heart comprising pixels.

4. The method as claimed in claim 3, further comprising:
   identifying the pixels that represent coronary calcification in a slice image of the 3D image data record.

5. The method as claimed in claim 4, wherein mutually adjacent pixels that represent coronary calcification are interconnected within a slice image and across slice images, or are associated with one another, and form at least one spatial accumulation of pixels that represent coronary calcification.

6. The method as claimed in claim 5, wherein pixels that are at a distance of between one and thirty pixels from an initial pixel that represents coronary calcification are in the neighborhood of the initial pixel.

7. The method as claimed in claim 6, further comprising:
prescribing a distance range of pixels around an initial pixel that represents coronary calcification, in which further pixels that represent coronary calcification should be sought after.

8. The method as claimed in claim 5, wherein a spatial profile of the at least one accumulation of pixels that represent coronary calcification and the at least one 3D model of the profile of the coronary vessels in a human are related to one another or are compared to one another.

9. The method as claimed in claim 8, wherein the at least one accumulation of pixels that represent coronary calcification is assigned to at least one coronary vessel in the at least one 3D model of the profile of the coronary vessels in a human on a basis of a similarity comparison between the spatial profile of the at least one accumulation of pixels that represent coronary calcification and the at least one 3D model of the profile of the coronary vessels in a human.

10. The method as claimed in claim 1, wherein the 3D image data record includes voxels and voxels representing coronary calcification in the 3D image data record of the heart in the patient are identified.

11. The method as claimed in claim 10, wherein mutually adjacent voxels that represent coronary calcification are interconnected, or are associated with one another, and form at least one spatial accumulation of voxels that represent coronary calcification.

12. The method as claimed in claim 11, wherein voxels that are at a distance of between one and thirty voxels from an initial voxel that represents coronary calcification are in the neighborhood of the initial voxel.

13. The method as claimed in claim 12, further comprising:
prescribing a distance range of voxels around an initial voxel that represents coronary calcification, in which further voxels that represent coronary calcification are sought.

14. The method as claimed in claim 11, wherein a spatial profile of the at least one accumulation of voxels that represent coronary calcification and the at least one 3D model of the profile of the coronary vessels in a human are related to one another or are compared to one another.

15. The method as claimed in claim 14, wherein the at least one accumulation of voxels that represent coronary calcification is assigned to at least one coronary vessel in the at least one 3D model of the profile of the coronary vessels in a human on a basis of a similarity comparison between the spatial profile of the at least one accumulation of voxels that represent coronary calcification and the at least one 3D model of the profile of the coronary vessels in a human.

16. The method as claimed in claim 1, wherein the at least one 3D model of the profile of the coronary vessels in a human and the identified coronary calcification in the patient are visualized, the coronary calcification being assigned to the at least one coronary vessel of the at least one 3D model of the profile of the coronary vessels in a human.

17. The method as claimed in claim 16, wherein a volume of coronary calcification per coronary vessel is established.

18. A device, comprising:
a storage unit configured to store a 3D image data record of a heart in a patient and a 3D model of a profile of coronary vessels in a human; and
a computational unit configured to
identify pixels representing coronary calcification based on a 3D image data record of the heart in the patient, the 3D image data record being previously generated by an imaging instrument without a contrast agent being administered to the patient,
determine spatial accumulation of the identified pixels,
generate at least one 3D model of a profile of the coronary vessels in a human including spatial coordinates of centerlines and enveloping curves of the coronary vessels, the at least one 3D model depicting a right coronary artery, a left coronary artery, a left circumflex artery and a left anterior descending artery of the heart, the at least one 3D model being generated on a basis of a multiplicity of 3D data records of hearts with coronary vessels generated from a number of humans, and
assign the determined spatial accumulation of the identified pixels representing coronary calcification to the at least one 3D model of the profile of the coronary vessels in a human for distinguishing between a single vessel disease (SVD), a two vessel disease (2VD), a three vessel disease (3VD) and a four vessel disease (4VD).

19. A non-transitory computer-readable medium including a computer program product, the computer program product comprising instructions, which when executed by a processor, causes the processor to perform functions including:
identifying pixels representing coronary calcification based on a 3D image data record of the heart in the patient, the 3D image data record being previously generated by an imaging instrument without a contrast agent being administered to the patient;
determining spatial accumulation of the identified pixels;
generating at least one 3D model of a profile of the coronary vessels in a human including spatial coordinates of centerlines and enveloping curves of the coronary vessels, the at least one 3D model depicting a right coronary artery, a left coronary artery, a left circumflex artery and a left anterior descending artery of the heart, the at least one 3D model being generated on a basis of a multiplicity of 3D data records of hearts with coronary vessels generated from a number of humans; and
assigning the determined spatial accumulation of the identified pixels representing coronary calcification to the at least one 3D model of the profile of the coronary vessels in a human for distinguishing between a single vessel disease (SVD), a two vessel disease (2VD), a three vessel disease (3VD) and a four vessel disease (4VD).

20. The method as claimed in claim 3, wherein mutually adjacent pixels that represent coronary calcification are interconnected within a slice image and across slice images, or are associated with one another, and form at least one spatial accumulation of pixels that represent coronary calcification.

* * * * *